(12) United States Patent
Mazza

(10) Patent No.: US 8,507,844 B2
(45) Date of Patent: Aug. 13, 2013

(54) TECHNIQUES FOR SAMPLE ANALYSIS

(75) Inventor: Cecilia B. Mazza, Vollsjö (SE)

(73) Assignee: Waters Technologies Corporation, Milford, MA (US)

( * ) Notice: Subject to any disclaimer, the term of this patent is extended or adjusted under 35 U.S.C. 154(b) by 80 days.

(21) Appl. No.: 13/208,406

(22) Filed: Aug. 12, 2011

(65) Prior Publication Data

US 2012/0205532 A1  Aug. 16, 2012

Related U.S. Application Data

(60) Provisional application No. 61/378,620, filed on Aug. 31, 2010.

(51) Int. Cl.
*B01D 59/44* (2006.01)
*H01J 49/26* (2006.01)
*G01N 27/64* (2006.01)

(52) U.S. Cl.
USPC ............ 250/282; 250/281; 250/284; 250/288

(58) Field of Classification Search
USPC .................. 436/541; 250/281, 282, 288, 290
See application file for complete search history.

(56) References Cited

U.S. PATENT DOCUMENTS

| | | | | |
|---|---|---|---|---|
| 5,364,795 A | * | 11/1994 | Sausa et al. | 436/106 |
| 5,448,062 A | * | 9/1995 | Cooks et al. | 250/288 |
| 5,523,566 A | * | 6/1996 | Fuerstenau et al. | 250/282 |
| 5,854,084 A | * | 12/1998 | Drukier et al. | 436/541 |
| 6,124,592 A | * | 9/2000 | Spangler | 250/287 |
| 6,225,132 B1 | * | 5/2001 | Drukier et al. | 436/541 |
| 6,426,226 B1 | * | 7/2002 | Senkan | 506/11 |
| 6,727,498 B2 | * | 4/2004 | Fries et al. | 250/288 |
| 6,744,045 B2 | * | 6/2004 | Fries et al. | 250/288 |
| 6,806,463 B2 | * | 10/2004 | Miller et al. | 250/286 |
| 6,815,669 B1 | * | 11/2004 | Miller et al. | 250/286 |
| 6,865,926 B2 | * | 3/2005 | O'Brien et al. | 73/23.27 |
| 7,057,168 B2 | * | 6/2006 | Miller et al. | 250/287 |
| 7,075,068 B2 | * | 7/2006 | Miller et al. | 250/290 |
| 7,078,679 B2 | * | 7/2006 | Westphall et al. | 250/287 |
| 7,161,145 B2 | * | 1/2007 | Oser et al. | 250/288 |
| 7,217,920 B2 | * | 5/2007 | Miller et al. | 250/287 |
| 7,223,970 B2 | * | 5/2007 | Miller et al. | 250/291 |
| 7,241,989 B2 | * | 7/2007 | Miller et al. | 250/282 |
| 7,332,345 B2 | * | 2/2008 | Darrach et al. | 436/173 |
| 7,355,170 B2 | * | 4/2008 | Miller et al. | 250/287 |
| 7,388,195 B2 | * | 6/2008 | Zapata et al. | 250/288 |
| 7,453,060 B2 | * | 11/2008 | Miller et al. | 250/288 |
| 7,462,825 B2 | * | 12/2008 | Miller et al. | 250/288 |
| 7,518,108 B2 | * | 4/2009 | Frey et al. | 250/288 |
| 7,530,257 B2 | * | 5/2009 | Bonne | 73/23.25 |

(Continued)

OTHER PUBLICATIONS

Batt, Angela L. et al; "Analysis of Ecologically Relevant Pharmaceuticals in Wastewater and Surface Water Using Selective Solid-Phase Extraction and UPLC-MS/MS"; Anal. Chem. 2008, 80, 5021-5030.

*Primary Examiner* — David A Vanore
(74) *Attorney, Agent, or Firm* — Muirhead and Saturnelli, LLC

(57) ABSTRACT

Techniques are described for performing sample analysis. Liquid chromatographic separation of a sample is performed and an eluent is generated. Mass spectrometry on said eluent is performed to detect a compound where the compound may occur in trace amounts. The compound may have a concentration, for example, of approximately less than one part per trillion.

24 Claims, 3 Drawing Sheets

(56) References Cited

U.S. PATENT DOCUMENTS

| | | | |
|---|---|---|---|
| 7,576,319 B2 * | 8/2009 | Miller et al. | 250/282 |
| 7,608,818 B2 * | 10/2009 | Miller et al. | 250/288 |
| 7,619,214 B2 * | 11/2009 | Miller et al. | 250/288 |
| 7,621,171 B2 * | 11/2009 | O'Brien | 73/23.41 |
| 7,968,842 B2 * | 6/2011 | Zapata et al. | 250/288 |
| 7,977,629 B2 * | 7/2011 | McEwen et al. | 250/288 |
| 8,003,935 B2 * | 8/2011 | Robinson et al. | 250/288 |
| 8,003,936 B2 * | 8/2011 | Robinson et al. | 250/288 |
| 8,247,784 B2 * | 8/2012 | Neidholdt et al. | 250/423 R |
| 8,334,505 B2 * | 12/2012 | Robinson et al. | 250/288 |
| 2004/0169137 A1 * | 9/2004 | Westphall et al. | 250/281 |
| 2009/0095901 A1 * | 4/2009 | Robinson et al. | 250/283 |
| 2010/0264304 A1 * | 10/2010 | Pablo et al. | 250/282 |
| 2012/0003748 A1 * | 1/2012 | Robinson et al. | 436/173 |
| 2012/0325024 A1 * | 12/2012 | Vidal-de-Miguel et al. | 73/863.24 |

* cited by examiner

TECHNIQUES FOR SAMPLE ANALYSIS

RELATED APPLICATION

This application claims the benefit of U.S. Provisional application Ser. No. 61/378,620, filed Aug. 31, 2010, the entire disclosure of which is incorporated herein by this reference.

TECHNICAL FIELD

This application generally relates to techniques for sample analysis and detecting compounds of interest.

BACKGROUND INFORMATION

Mass spectrometry (MS) is used widely for identifying and quantifying molecular species in a sample. During analysis, molecules from the sample are ionized to form ions. A detector produces a signal relating to the mass of the molecule and charge carried on the molecule and a mass-to-charge ratio (m/z) for each of the ions is determined.

A chromatographic separation technique may be performed prior to injecting the sample into a mass spectrometer. Chromatography is a technique for separating compounds, such as those held in solution, where the compounds will exhibit different affinity for a separation medium in contact with the solution. As the solution flows through such an immobile medium, the compounds separate from one another. Common chromatographic separation instruments include gas chromatographs (GC) and liquid chromatographs (LC). When coupled to a mass spectrometer, the resulting systems are referred to as GC/MS or LC/MS systems. GC/MS or LC/MS systems are typically on-line systems in which the output of the GC or LC is coupled directly to the MS.

In an LC/MS system, a sample is injected into the liquid chromatograph at a particular time. The liquid chromatograph causes the sample to elute over time resulting in an eluent that exits the liquid chromatograph. The eluent exiting the liquid chromatograph is continuously introduced into the ionization source of the mass spectrometer. As the separation progresses, the composition of the mass spectrum generated by the MS evolves and reflects the changing composition of the eluent.

Typically, at regularly spaced time intervals, a computer-based system samples and records the spectrum. The response (or intensity) of an ion is the height or area of the peak as may be seen in the spectrum. The spectra generated by conventional LC/MS systems may be further analyzed. Mass or mass-to-charge ratio estimates for an ion are derived through examination of a spectrum that contains the ion. Retention time estimates for an ion are derived by examination of a chromatogram that contains the ion.

Two stages of mass analysis (MS/MS also referred to as tandem mass spectrometry) may also be performed. One particular mode of MS/MS is known as product ion scanning where parent or precursor ions of a particular m/z value are selected in the first stage of mass analysis by a first mass filter/analyzer. The selected precursor ions are then passed to a collision cell where they are fragmented to produce product or fragment ions. The product or fragment ions are then mass analyzed by a second mass filter/analyzer.

In connection with performing sample analysis, it may be desirable to detect a compound of interest where the compound may have a very low level of concentration in the sample.

SUMMARY OF THE INVENTION

In accordance with one aspect of the invention is a method of performing sample analysis comprising: performing liquid chromatographic separation of a sample and generating an eluent; and performing mass spectrometry on said eluent to detect a compound, wherein the compound has a concentration of approximately less than one part per trillion. The method may be performed in connection with a food-related industry or an environmental-related industry. The sample may be obtained from any of a solid, a liquid, a food, a solid food, a liquid food, water, sludge, soil, fish tissue, animal tissue, a plant, a vegetable, a fruit, milk, honey, juice, and bird tissue. The sample may be obtained from any of drinking water, surface water, ground water, and wastewater. The method may also include concentrating the sample by performing solid phase extraction prior to said liquid chromatographic separation. The solid phase extraction may be performed using a cartridge. At least one other sample processing step may be performed prior to said solid phase extraction. The compound may be any of a pharmaceutical, personal care product, endocrine disruptor, drug, and pesticide. The compound may be any of cimetedine, ranitidine, trimethoprim, sulfamethoxazole, 10-hydroxy-amitriptyline, promethazine, paroxetine, alprazolam, amitriptyline, benztropine, norfluoxetine, fluoxetine, desmethylsertraline, sertraline, albuterol, atenolol, clonidine, oxycodone, amphetamine, hydrocodone, triamterene, metoprolol, enalipril, propanolol, desmethyldiltiazem, diltiazem, norverapamil, verapamil, propoxyphene, amlodipine, acetaminophen, prednisone, prednisolone, hydrocortisone, carbamazepine, betamethasone, methylprednisolone, norethindrone, testosterone, valsartan, fluocinonide, atrovastatin, fluticasone, progesterone, simvastatin, theophylline, hydrochiorothiazide, 2-hydroxy-ibuprofen, furosemide, warfarin, glipizide, ibuprofen, gemfibrozil. glyburide, chlorpheniramine, tripolidine, dextromethorphan, clomitrazole, propranolol, erythromycin, terbinafine, azithromycin, miconazole, tramadol, trimethoprim, cocaine, codeine, diphenihydramine, amphetamine, tetracycline, oxytetracycline, sulfanilamide, sulfathiazole, lincomycin, cefatoxime, carbadox, ciprofloxacin, enrofloxacin, penicillin G, oxacillin, naproxen, triclosan, and atrazine. Mass spectrometry may be performed by a triple quadrupole mass spectrometer.

In accordance with another aspect of the invention is a system for performing sample analysis comprising: a liquid chromatograph that perform chromatographic separation of a sample and generates an eluent; and a mass spectrometer that analyzes said eluent to detect a compound, wherein the compound has a concentration of approximately less than one part per trillion. The compound may be any of a pharmaceutical, personal care product, endocrine disruptor, drug, and pesticide. The compound may be any of cimetedine, ranitidine, trimethoprim, sulfamethoxazole, 10-hydroxy-amitriptyline, promethazine, paroxetine, alprazolam, amitriptyline, benztropine, norfluoxetine, fluoxetine, desmethylsertraline, sertraline, albuterol, atenolol, clonidine, oxycodone, amphetamine, hydrocodone, triamterene, metoprolol, enalipril, propanolol, desmethyldiltiazem, diltiazem, norverapamil, verapamil, propoxyphene, amlodipine, acetaminophen, prednisone, prednisolone, hydrocortisone, carbamazepine, betamethasone, methylprednisolone, norethindrone, testosterone, valsartan, fluocinonide, atrovastatin, fluticasone, progesterone, simvastatin, theophylline, hydrochiorothiazide, 2-hydroxy-ibuprofen, furosemide, warfarin, glipizide, ibuprofen, gemfibrozil. glyburide, chlorpheniramine, tripolidine, dextromethorphan, clomitrazole, propranolol, erythromycin, terbinafine, azithromycin, miconazole, tramadol, trimethoprim, cocaine, codeine, diphenhydramine, amphetamine, tetracycline, oxytetracycline, sulfanilamide, sulfathiazole, lincomycin, cefatoxime, carbadox, ciprofloxacin, enrofloxacin, penicillin G, oxacillin, naproxen, triclosan, and atrazine. The sample may be obtained from any of a solid, a liquid, a food, a solid food, a liquid food, water, sludge, soil, fish tissue, animal tissue, a plant, a vegetable, a fruit, milk, honey, juice, and bird tissue. The sample may be obtained from any of drinking water, surface water, ground water, and wastewater. The sample may be concentrated by performing solid phase extraction prior to processing by said liquid chromatograph.

In accordance with another aspect of the invention is a method of performing sample analysis comprising: performing processing of a source sample, said processing including performing solid phase extraction to obtain a concentrated liquid sample; performing liquid chromatographic separation of concentrated liquid sample and generating an eluent; and performing tandem mass spectral analysis of said eluent to detect a compound, wherein the compound has a concentration of approximately less than or equal to one part per trillion. The compound may be any of a pharmaceutical, personal care product, endocrine disruptor, drug, herbicide, and pesticide. The compound may be any of cimetedine, ranitidine, trimethoprim, sulfamethoxazole, 10-hydroxy-amitriptyline, promethazine, paroxetine, alprazolam, amitriptyline, benztropine, norfluoxetine, fluoxetine, desmethylsertraline, sertraline, albuterol, atenolol, clonidine, oxycodone, amphetamine, hydrocodone, triamterene, metoprolol, enalipril, propanolol, desmethyldiltiazem, diltiazem, norverapamil, verapamil, propoxyphene, amlodipine, acetaminophen, prednisone, prednisolone, hydrocortisone, carbamazepine, betamethasone, methylprednisolone, norethindrone, testosterone, valsartan, fluocinonide, atrovastatin, fluticasone, progesterone, simvastatin, theophylline, hydrochiorothiazide, 2-hydroxy-ibuprofen, furosemide, warfarin, glipizide, ibuprofen, gemfibrozil. glyburide, chlorpheniramine, tripolidine, dextromethorphan, clomitrazole, propranolol, erythromycin, terbinafine, azithromycin, miconazole, tramadol, trimethoprim, cocaine, codeine, diphenhydramine, amphetamine, tetracycline, oxytetracycline, sulfanilamide, sulfathiazole, lincomycin, cefatoxime, carbadox, ciprofloxacin, enrofloxacin, penicillin G, oxacillin, naproxen, triclosan, and atrazine. The source sample may be any of a solid, a liquid, a food, a solid food, a liquid food, water, sludge, soil, fish tissue, animal tissue, a plant, a vegetable, a fruit, milk, honey, juice, and bird tissue. The source sample may be any of drinking water, surface water, ground water, and wastewater.

In accordance with another aspect of the invention is a method of performing sample analysis comprising: performing processing of a source sample, said processing including performing solid phase extraction to obtain a concentrated liquid sample, said source sample being other than a water sample; performing liquid chromatographic separation of the concentrated liquid sample and generating an eluent; and performing tandem mass spectral analysis of said eluent to detect a compound, wherein the compound has a concentration of approximately less than ten parts per trillion. The concentration may be approximately within the range of two to ten parts per trillion. The method may be performed in connection with a food-related industry or in connection with an environmental-related industry. The compound may be any of a metabolite, natural product, and organic compound. The source sample may include a plurality of compounds including said compound. Each of the plurality of compounds may be any of a metabolite, natural product, and organic compound detected by said performing tandem mass spectral analysis, each of said plurality of compounds having a concentration of approximately less than or equal to one part per trillion. The source sample may include a plurality of compounds each detected by performing said tandem mass spectral analysis. Each of the plurality of compounds may have a concentration of approximately less than or equal to one part per trillion. At least one of the plurality of compounds may be any of cimetedine, ranitidine, trimethoprim, sulfamethoxazole, 10-hydroxy-amitriptyline, promethazine, paroxetine, alprazolam, amitriptyline, benztropine, norfluoxetine, fluoxetine, desmethylsertraline, sertraline, albuterol, atenolol, clonidine, oxycodone, amphetamine, hydrocodone, triamterene, metoprolol, enalipril, propanolol, desmethyldiltiazem, diltiazem, norverapamil, verapamil, propoxyphene, amlodipine, acetaminophen, prednisone, prednisolone, hydrocortisone, carbamazepine, betamethasone, methylprednisolone, norethindrone, testosterone, valsartan, fluocinonide, atrovastatin, fluticasone, progesterone, simvastatin, theophylline, hydrochiorothiazide, 2-hydroxy-ibuprofen, furosemide, warfarin, glipizide, ibuprofen, gemfibrozil. glyburide, chlorpheniramine, tripolidine, dextromethorphan, clomitrazole, propranolol, erythromycin, terbinafine, azithromycin, miconazole, tramadol, trimethoprim, cocaine, codeine, diphenhydramine, amphetamine, tetracycline, oxytetracycline, sulfanilamide, sulfathiazole, lincomycin, cefatoxime, carbadox, ciprofloxacin, enrofloxacin, penicillin G, oxacillin, naproxen, triclosan, and atrazine.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

Figure 1:
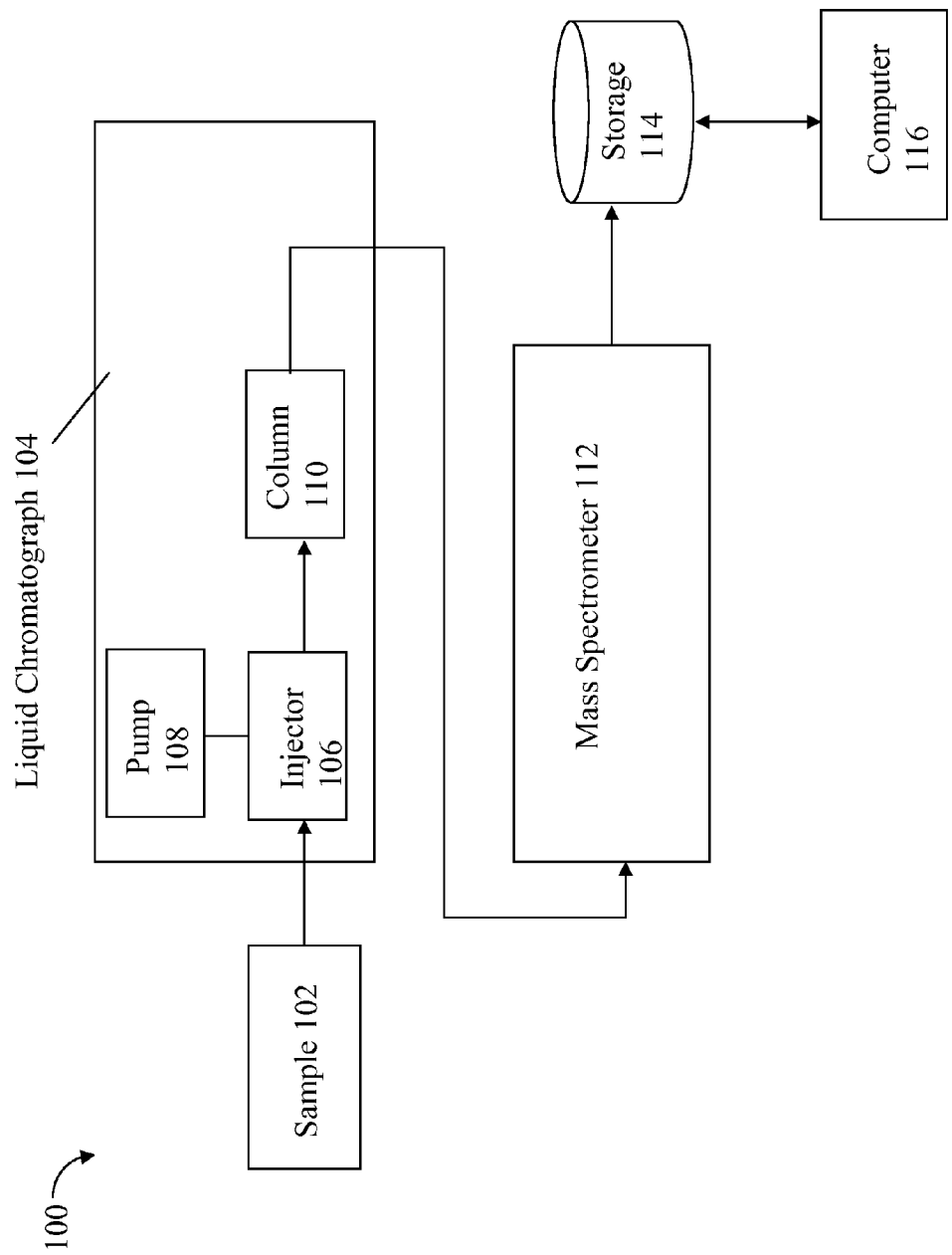
FIG. 1 is a block diagram of a system in accordance with one embodiment of the techniques herein.

As used herein, the following terms generally refer to the indicated meanings:

"Chromatography"—refers to equipment and/or methods used in the separation of chemical compounds. Chromatographic equipment typically moves fluids and/or ions under pressure and/or electrical and/or magnetic forces. The word "chromatogram," depending on context, herein refers to data or a representation of data derived by chromatographic means. A chromatogram can include a set of data points, each of which is composed of two or more values; one of these values is often a chromatographic retention time value, and the remaining value(s) are typically associated with values of intensity or magnitude, which in turn correspond to quantities or concentrations of components of a sample. In connection with techniques herein, the sample may contain one or more compounds of interest. A compound of interest may be a small molecule, such as an organic compound, metabolite, and the like. Small molecules may refer to low molecular weight organic compounds.

Retention time—in context, typically refers to the point in a chromatographic profile at which an entity reaches its maximum intensity.

Ions—A compound, for example, that is typically detected using the mass spectrometer (MS) appears in the form of ions in data generated as a result of performing an experiment in an LC/MS system. An ion has, for example, a retention time and an m/z value. The LC/MS system may be used to perform experiments and produce a variety of observed measurements for every detected ion. This includes: the mass-to-charge ratio (m/z), mass (m), the retention time, and the signal intensity of the ion, such as a number of ions counted.

Generally, an LC/MS system may be used to perform sample analysis and may provide an empirical description of, for example, a small molecule such as a pharmaceutical or herbicide in terms of its mass, charge, retention time, and total intensity. When a small molecule elutes from a chromatographic column, it elutes over a specific retention time period and reaches its maximum signal at a single retention time. After ionization and (possible) fragmentation, the compound appears as a related set of ions.

In an LC/MS separation, a small molecule will produce a single charged state. MS/MS may also be referred to as tandem mass spectrometry which can be performed in combination with LC separation (e.g., denoted LC/MS/MS).

Techniques and embodiments will now be described with reference to exemplary methods and apparatus for analyzing samples such as may be for sample analyses in a system performing LC/MS/MS. It will be appreciated that the techniques described herein may be used in connection with other embodiments and have broader application for analysis of other compounds than those that may be provided and listed herein. For example, an embodiment may perform other techniques in connection with separation processing, use other suitable instruments different than those particular ones mentioned herein having the required capabilities and functionalities, and the like.

As set forth in following paragraphs, techniques are described which provide for detection of compounds of interest in a sample where the compounds may have very low levels of concentration in trace amounts. For example, techniques described herein may be used to detect one or more compounds of concern having concentrations of one part per trillion (ppt) or lower. The compounds of concern may include, for example, pharmaceutical and personal care products, endocrine disruptors, drugs, pesticides, herbicides, and the like. Personal care products may generally refer to personal consumer products, including toiletries, used for beautification, personal hygiene, and the like and may include, for example, facial cleansers, shampoo and other hair products, cosmetics, and the like. The compounds of concern may occur in samples which are liquids and/or solids such as, for example, water samples (e.g., ground water, surface water, wastewater), food solids (e.g., fish), soil, sludge, plants, animal tissue, food liquids (e.g., milk, honey, juices), and the like. The techniques herein may be used in connection with a variety of different markets or industry-related areas such as the food and environmental markets. For example, the techniques herein may be used for detecting compounds of interest in a sample in connection with a regulation in the food industry, environmental-related industry such as water treatment, and the like.

Referring to FIG. 1, shown is an embodiment of a system in accordance with techniques herein. The system 100 includes a liquid chromatograph (LC) 104, mass spectrometer (MS) 112, storage 114, and computer 116. As will be described in following paragraphs, the system 100 may be used to perform analysis of sample 102 for detecting one or more compounds of interest. The LC 104 may include an injector 106 that receives sample 102, a pump 108, and a column 110. The liquid sample 102 may be a liquid. As will be described in following paragraphs, the liquid sample 102 introduced as an input to the LC 104 may have been obtained from another original or source sample. The liquid sample 102 may have been produced as a result of performing other sample preparation processing (e.g., offline and/or online processing of the original sample). The particular preparation processing may vary with the original or source sample. For example, different preparation processing may be performed to a source sample that is a solid, such as fish tissue, than with respect to a source sample that is a water sample, such as wastewater. This is described in more detail in following paragraphs although generally any suitable method of sample preparation processing may be used in connection with the techniques herein.

In operation, the sample 102 is injected into the LC 104 via the injector 106. The pump 108 pumps the sample through the column 110 to separate the sample into component parts according to retention time through the column 110. A high pressure stream of chromatographic solvent provided by pump 108 and injector 106 forces sample 102 to migrate through a chromatographic column 110 in liquid chromatograph 104. Column 110 typically comprises a packed column of silica beads whose surface comprises bonded molecules. The output from the column 110 is input to MS 112 for analysis. Although not illustrated, the MS 112 may include components such as a desolvation/ionization device, collision cell, mass analyzer, a detector, and the like. In one embodiment, the LC 104 may be an ultra performance liquid chromatography (HPLC) system such as the ACQUITY HPLC® System from Waters Corporation of Milford, Mass.

Mass analyzers of the MS 112 can be placed in tandem in a variety of configurations, including, e.g., quadrupole time-of-flight (Q-TOF) mass analyzers. A tandem configuration enables on-line collision modification and analysis of an already mass-analyzed molecule. For example, in triple quadrupole based massed analyzers (such as Q1-Q2-Q3 or Q1-Q2-TOF mass analyzers), the second quadrupole (Q2), imports accelerating voltages to the ions separated by the first quadrupole (Q1). These ions, collide with a gas expressly introduced into Q2. The ions fragment as a result of these collisions. Those fragments are further analyzed by the third quadrupole (Q3) or by the TOF. In one embodiment the MS 112 may be the Xevo™ TQ MS or Xevo™ TQ-S from Waters Corporation of Milford, Mass.

As an output, the MS 112 generates a series of spectra or scans collected over time. A mass-to-charge spectrum is intensity plotted as a function of m/z. Each element, a single mass-to-charge ratio, of a spectrum may be referred to as a channel. Viewing a single channel over time provides a chromatogram for the corresponding mass-to-charge ratio. The generated mass-to-charge spectra or scans can be acquired and recorded on a storage medium such as a hard-disk drive or other storage media represented by element 114 that is accessible to computer 118. Typically, a spectrum or chromatogram is recorded as an array of values and stored on storage 114. The spectra stored on 114 may be accessed using the computer 116 such as for display, subsequent analysis, and the like. A control means (not shown) provides control signals for the various power supplies (not shown) which respectively provide the necessary operating potentials for the components of the system 100 such as the MS 112. These control signals determine the operating parameters of the instrument.

The control means is typically controlled by signals from a computer or processor, such as the computer 116.

A molecular species migrates through column 110 and emerges, or elutes, from column 110 at a characteristic time. This characteristic time commonly is referred to as the molecule's retention time. Once the molecule elutes from column 106, it can be conveyed to the MS 112. A retention time is a characteristic time. That is, a molecule that elutes from a column at retention time t in reality elutes over a period of time that is essentially centered at time t. The elution profile over the time period is referred to as a chromatographic peak. The elution profile of a chromatographic peak can be described by a bell-shaped curve. The peak's bell shape has a width that typically is described by its full width at half height, or half-maximum (FWHM). The molecule's retention time is the time of the apex of the peak's elution profile. Spectral peaks appearing in spectra generated by mass spectrometers have a similar shape and can be characterized in a similar manner.

The storage 114 may be any one or more different types of computer storage media and/or devices. As will be appreciated by those skilled in the art, the storage 114 may be any type of computer-readable medium having any one of a variety of different forms including volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, (DVD) or other optical storage, magnetic cassettes, magnetic tape, magnetic disk storage or other magnetic storage devices, or any other medium which can be used to store the desired code, data, and the like, which can accessed by a computer processor.

The computer 116 may be any commercially available or proprietary computer system, processor board, ASIC (application specific integrated circuit), or other component which includes a computer processor configured to execute code stored on a computer readable medium. The processor, when executing the code, may cause the computer system 116 to perform processing steps such as to access and analyze the data stored on storage 114. The computer system, processor board, and the like, may be more generally referred to as a computing device. The computing device may also include, or otherwise be configured to access, a computer readable medium, such as represented by 114, comprising executable code stored thereon which cause a computer processor to perform processing steps.

The system 100 may be used to perform LC/MS/MS on a sample and generate mass spectra for precursor and its product or fragment ions of at least one compound in the sample. The generated mass spectra may be further analyzed and/or processed for use in connection with any of a variety of techniques for different applications. In connection with the techniques herein, the mass spectra data may be examined to determine a precursor and its associated product ions. Once the precursor and its associated product ions have been determined, such information may be used to identify a particular compound of interest. For example, information may be contained in a database for a compound of interest which is known and identified by the occurrence of a precursor and one or more product ions. The precursor and product ion information obtained from the mass spectra may be compared against a database of known precursor/product ion information for compounds.

Any suitable method using the system 100 may be used to obtain both precursor and product ions from a sample injection. Such methods provide effectively simultaneous mass analysis of both precursor and product ions. For example, a portion of an eluted precursor is fragmented to form product ions, and the precursor and product ions are substantially simultaneously analyzed, either at the same time or, for example, in rapid succession. One approach to such alternating, effectively simultaneous analysis, is described in U.S. Pat. No. 6,717,130 to Bateman, et al. ("Bateman"), which is incorporated herein by reference and describes application of an alternating voltage to a collision cell of the MS 112 to regulate fragmentation. Thus, an embodiment may use the technique described in the Bateman '130 patent or other suitable technique which may use retention-time observations to support the determination of which product ion(s) are derived from a particular precursor. The product ions are associated with their precursor ion in response to matching retention-time values.

Analysis of the mass spectra permits measurement of an accurate retention time value for both the eluted precursor and its associated product(s) or fragment(s). Moreover, for example, peak shape, width, and/or retention time of the peaks associated with precursor ions and with product ions may be compared to determine which product ions are associated with a particular precursor ion. The product ions are associated with their precursor ion in response to matching retention-time values and/or other characteristics such as chromatographic peak profile or shape as described elsewhere herein. Furthermore and more generally, ions (precursors and fragments) derived from a common originating molecule may have a common retention time and/or other similar characteristics.

For example, a threshold retention-time difference is selected; if the difference in retention times of a product ion and a precursor ion is less than the threshold value, the product is determined to be derived from the precursor. For example, one suitable threshold value is equal to one tenth the retention-time peak width of the precursor ion. The retention-time value of an ion is optionally defined as the time value of the peak maximum of the peak that was observed for that ion.

In an LC/MS experiment as mentioned above, an ion can be described and/or referred to by its retention time, mass-to-charge ratio or mass, charge state, and intensity. An originating molecule can give rise to multiple ions derived from the originating molecule where each such ion is either a precursor or a fragment. These fragments arise from processes that break up the originating molecule. These processes can occur in the ionization source or in a collision cell of the MS 112. Because fragment ions derive from a common eluting, originating molecule, they must have the same chromatographic retention time and peak profile as the originating molecule. The retention time and peak shapes of ions that derive from a common originating molecule are the same because the time of ion formation, fragmentation, and ion detection is generally much shorter than the peak width of the originating molecule. For example, a typical chromatographic peak width, measured at full-width at half-maximum (FWHM) is 5 to 30 seconds. The time of ion formation, fragmentation, and detection is typically sub milliseconds. Thus on a chromatographic time scale, the time of ion formation is an instantaneous process. It follows that differences in observed retention times of the ions that derived from an originating molecule is effectively zero. That is, sub-millisecond retention time differences between ions that derived from an originating molecule are small compared to the chromatographic peak width.

With respect to ions that are generated from collision-induced disassociation of intact precursor ions, the fragment or product ions are associated with their parent precursor ion. By using the mass spectrometer in a high-low data acquisition mode (also referred to herein as an elevated-low-data acquisition mode) as described in the Bateman '130 patent, this association is accomplished without requiring the instrument to pre-select a single precursor for subsequent fragmentation. More specifically, associated ions are appropriately grouped when multiple precursors are fragmenting simultaneously, at essentially the same retention time.

The retention time and chromatographic peak profile of a molecule (such as, for example, a small molecule, metabolite, natural product in connection with techniques herein) eluting from a chromatographic support matrix, such as column 110, is a function of the physical interaction of that molecule between the support matrix and mobile phase. The degree of interaction that a molecule has between the support matrix and the mobile phase dictates the chromatographic profile and retention time for that molecule. In a complex mixture, each molecule is chemically different. As a result, each molecule can have a different affinity for the chromatographic matrix and the mobile phase. Consequently, each can exhibit a unique chromatographic profile.

Generally, a chromatographic profile for a specific molecule is unique and describes the physicochemical properties of that molecule. Parameters optionally used to characterize the chromatographic peak profile of a given molecule include the time of initial detection (liftoff), normalized slope, the time of inflection points relative to the time of the peak apex, the time of maximum response (peak apex), the peak width, at inflection points, at full-width-at-half-maximum (FWHM), peak shape asymmetry, and the time of the final detection (touch down) to name only a few.

Figure 2:
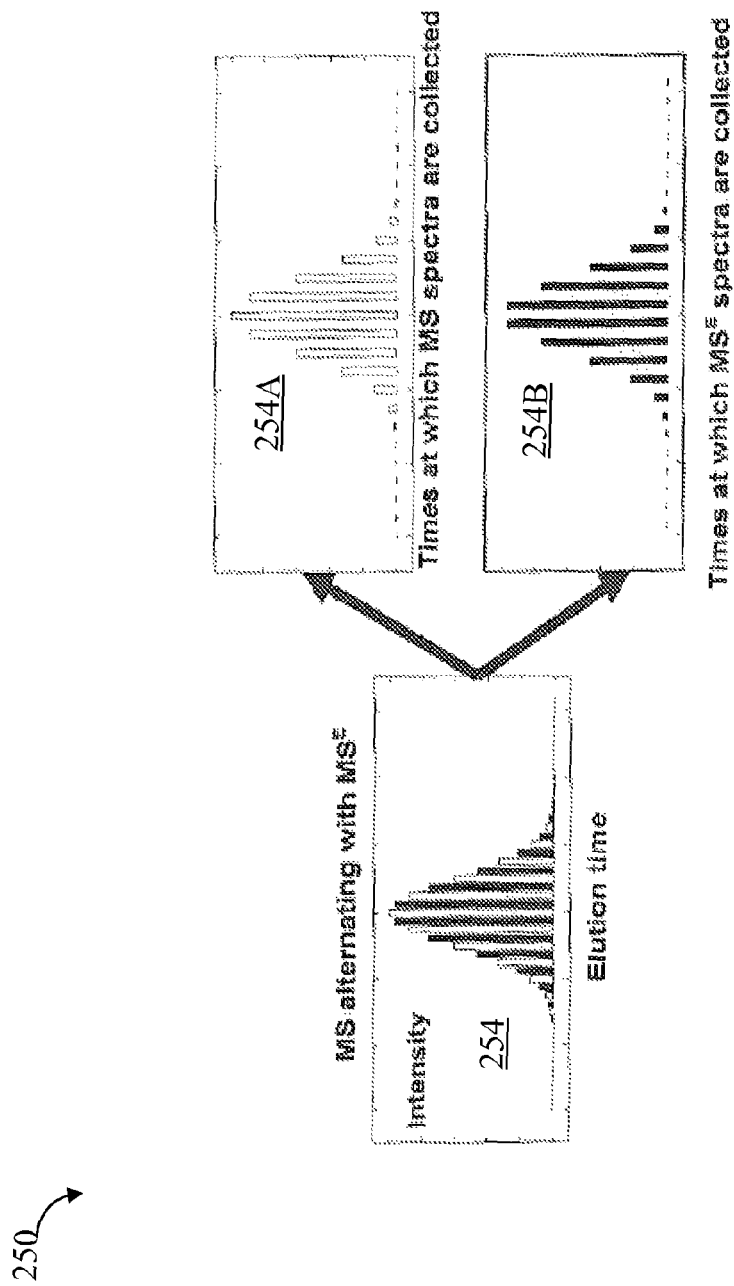
FIG. 2 shows three related graphs, which illustrate the collection of mass spectra in accordance with one embodiment of the techniques herein.

FIG. 2 shows three related graphs that illustrate the collection of mass spectra during a period of time that covers an eluted peak of a precursor, according to one embodiment of the invention. A first graph 254 illustrates the alternating collection over elution time of low-energy spectra (i.e., spectra from unfragmented precursors, labeled "MS") and elevated-energy spectra (i.e., spectra from fragmented precursors, that is, product ions, labeled "$MS^E$".) Second and third graphs 254A, 254B respectively illustrate the MS and $MS^E$ spectral collection times and the reconstruction of the retention time peak associated with the precursor as may be generated using the alternating scanning technique described in the Bateman '130 patent.

The reconstructed peak represents the chromatographic elution profile of a single precursor. The horizontal axis corresponds to elution time of the peak profile. The vertical axis corresponds to arbitrary units of intensity associated with the time-varying concentration of the precursor as it elutes from the chromatographic column.

An eluting precursor, passed to the mass spectrometer, thus produces ions in both low- and elevated-energy modes. The ions produced in the low-energy mode are primarily those of the precursor ions in possibly different isotopic and charge states. In elevated-energy mode, the ions are primarily different isotopes and charge states of the fragment, or product, ions of those precursors. High-energy mode can also be referred to as elevated-energy mode.

In the graph 254, the alternating white and black bars thus represent the times at which spectra are collected with low and high (or elevated)-energy voltages of the eluting chromatographic peak. The low-energy (LE) graph 254A depicts the times at which a low-energy voltage is applied in the collision cell 218, resulting in low-energy spectra. The high or elevated energy (EE) graph 254B depicts the times at which an elevated-energy voltage is applied in the collision cell 218, resulting in elevated-energy spectra.

In connection with techniques described herein, an embodiment may determine masses of particular precursors of interest using a variety of different techniques. For example, in one embodiment utilizing the Bateman techniques as described elsewhere herein, the low energy (LE) cycle or mode may be used to generate spectra containing ions primarily from unfragmented precursors while the elevated-energy (EE) spectra contain ions primarily from fragmented precursors or product ions.

As mentioned above, the resulting LE and EE scan data produced as a result of sample analysis may be used to identify compounds of interest in the sample such as by comparing precursor and fragment information determined for a sample to information in a database regarding known compounds as identified by their associated precursor and fragment information. Such identification may be performed using any suitable technique.

As described above, the fluid sample 102 introduced to the LC 104 may be obtained from an original sample or source which has been processed using one or more sample preparation steps. The sample preparation processing may also vary with the particular source sample. In one embodiment, the original sample may be concentrated using a solid phase extraction (SPE) cartridge such as an OASIS® cartridge from Waters Corporation. For example, the cartridge may be a mixed mode reversed-phase/cation-exchange cartridge such as the OASIS® MCX cartridge. An embodiment in accordance with techniques herein may also use, for example, an OASIS® HLB, or OASIS® CX cartridge. If the source sample is a water sample, such as drinking water, surface water, ground water, or wastewater, the source sample may be concentrated using, for example, the OASIS® MCX cartridge by pouring the source sample directly into the cartridge. At a later point in time, a solvent may be introduced into the cartridge and the output stream may be used as the liquid sample 102 which is then introduced into the LC 104.

If the source sample is a water sample in combination with any particles or sediment such as, for example, soil, algae, and the like, additional processing (e.g., such as using a centrifuge) may be performed prior to concentrating using the cartridge in order to separate the liquid from the solid particles. Once separated, the supernatant liquid may then be introduced into the cartridge for concentration.

If the source sample is, for example, milk, juice, or honey, a solvent may be added to the source sample causing precipitation of a solid which may then be further processed, such as using a centrifuge, to separate the liquid from any solids. Once separated, the supernatant liquid may then be introduced into the cartridge for concentration.

If the source sample is a solid such as, for example, fish or animal tissue, a plant, vegetable, fruit, and the like, the solid may be ground up and mixed with a solvent for extraction of the compound of interest. The resulting mixture of ground solid particles and liquid (e.g., solvent with the extracted compound of interest) may be further processed, such as using a centrifuge, to separate the liquid from any solids. The supernatant liquid may then be introduced into the cartridge for concentration.

The foregoing are some examples of source sample processing that may be performed to generate the liquid sample 102 introduced into the LC 104. Generally, processing of an original or source sample may include any suitable processing that may vary with the particular source sample.

The techniques herein may generally be used to detect compounds of interest in a variety of different samples in connection with a variety of different markets or industry-related areas such as, for example, environmental (e.g. aquatic, ecological), and food markets. Such detection and associated quantification may be in accordance with regulations, standards, and/or other requirements. The compounds of interest may include compound classes such as, for example, pharmaceuticals, personal care products, endocrine disruptors, drugs (both legal and illegal/illicit), pesticides, and the like. Examples of compounds of interest that may be analyzed using techniques herein may include, for example, cimetedine, ranitidine, trimethoprim, sulfamethoxazole, 10-hydroxy-amitriptyline, promethazine, paroxetine, alprazolam, amitriptyline, benztropine, norfluoxetine, fluoxetine, desmethylsertraline, sertraline, albuterol, atenolol, clonidine, oxycodone, amphetamine, hydrocodone, triamterene, metoprolol, enalipril, propanolol, desmethyldiltiazem, diltiazem, norverapamil, verapamil, propoxyphene, amlodipine, acetaminophen, prednisone, prednisolone, hydrocortisone, carbamazepine, betamethasone, methylprednisolone, norethindrone, testosterone, valsartan, fluocinonide, atrovastatin, fluticasone, progesterone, simvastatin, theophylline, hydrochiorothiazide, 2-hydroxy-ibuprofen, furosemide, warfarin, glipizide, ibuprofen, gemfibrozil. glyburide, chlorpheniramine, tripolidine, dextromethorphan, clomitrazole, propranolol, erythromycin, terbinafine, azithromycin, miconazole, tramadol, trimethoprim, cocaine, codeine, diphenhydramine, amphetamine, tetracycline, oxytetracycline, sulfanilamide, sulfathiazole, lincomycin, cefatoxime, carbadox, ciprofloxacin, enrofloxacin, penicillin G, oxacillin, naproxen, triclosan, and atrazine. In connection with the foregoing list of exemplary compounds of interest, it should be noted that some single items may fall into multiple general or broader categories. For example, prednisone and testosterone may each be characterized as both an endocrine disruptor and a pharmaceutical.

The original or source samples may be liquids, solids, mixtures, and the like. Examples include, but are not limited to, any type of food, fish tissue, animal tissue, and plants. The food may include including any liquid food and solid food such as, for example, vegetables, fruits, milk, honey, and juice. Other examples of source samples may include soil, sludge, and water samples such as drinking water, surface water, ground water, and wastewater.

Using the techniques herein, the compounds of interest may be extracted from the source samples and detected in accordance with detection limits of approximately 1 ppt or lower. It should be noted that 1 ppt is equivalent to 1 nanogram/liter (ng/L). Such low levels of detection may be achieved using the techniques described above. In one embodiment, the liquid sample 102 introduced into the LC 104 may be a concentrated sample resulting from SPE. Generally, the techniques herein may be used to detect a compound of interest at a concentration of approximately less than 1 ppt. The techniques herein may also be used in connection with detection of slightly higher concentrations but still characterized as trace amounts. For example, the techniques herein may be used to detect compounds of interest in any source sample in accordance with detection limits of, for example, approximately less than 10 ppt, approximately between 2 ppt and 10 ppt, approximately between 1 ppt and 10 ppt.

Figure 3:
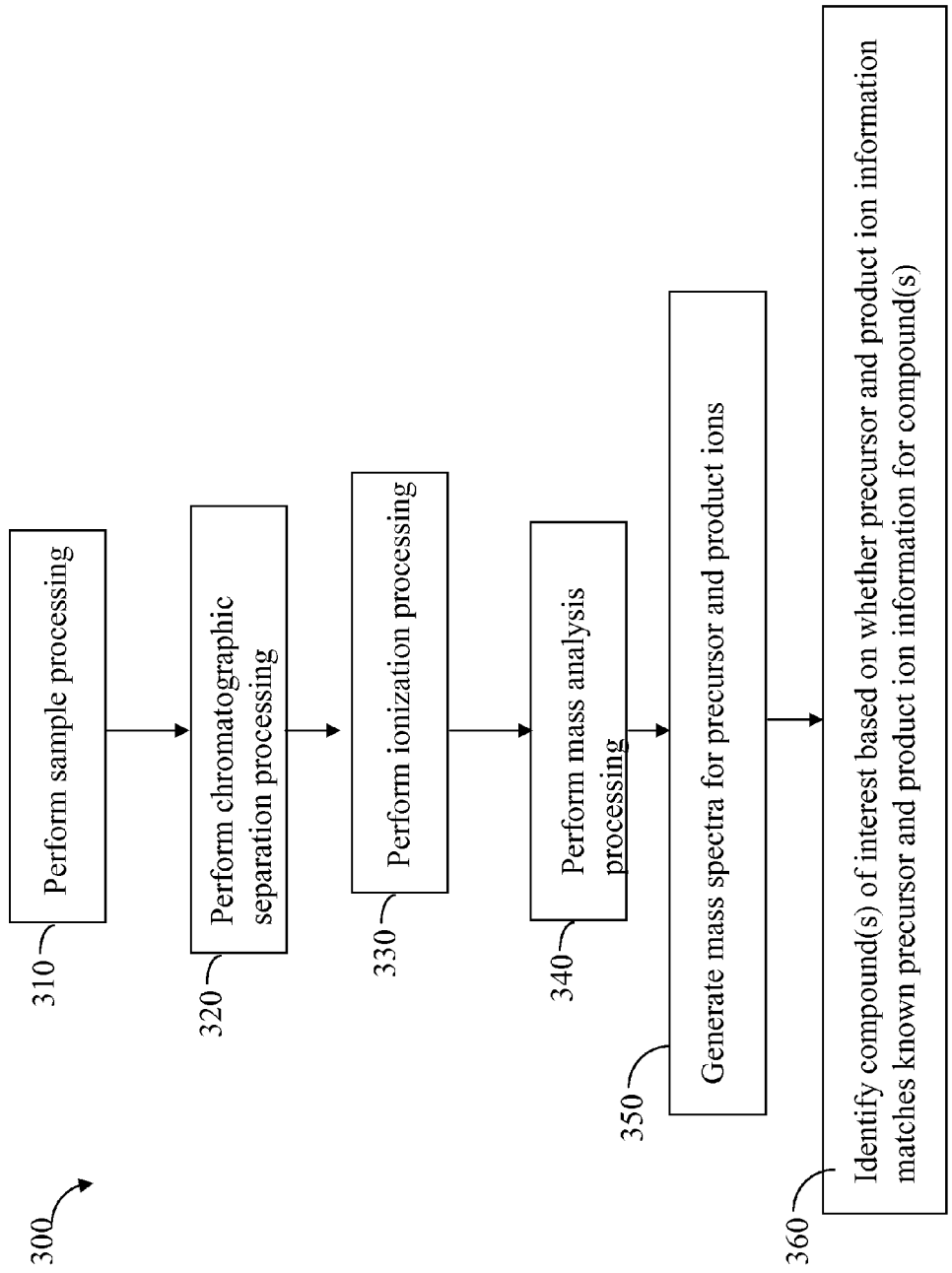
FIG. 3 is a flowchart of processing steps that may be performed in an embodiment in accordance with technique herein.

Referring to FIG. 3, shown is a flowchart of processing steps that may be performed in an embodiment in accordance with techniques herein. The steps of the flowchart 300 summarize processing described above with respect to an original or source sample being analyzed to detect one or more compounds of interest. At step 310, the source sample may be processed. Step 310 may include performing SPE to concentrate the source sample and obtain a liquid sample as introduced into the LC for processing. Step 310 may also include additional processing needed to obtain the liquid sample such as, for example, if the source sample is a solid. At step 320, chromatographic separation processing is performed for the liquid sample. Step 320 may be performed using an LC such as illustrated and described above in connection with FIG. 1. At step 330, ionization processing is performed with respect to the separated output from step 320. At step 340, mass analysis is performed. Steps 330 and 340 may be performed by an MS such as illustrated and described above in connection with FIG. 1. At step 350, mass spectra are generated for the precursor and associated product ions. The mass spectra of step 350 may be produced as an output of the MS. At step 360, the compound(s) of interest may be identified by determining whether the precursor and product ion information of step 350 matches known precursor and product ion information used to identify the compound(s). For example, a database may include precursor and product ion(s) identifying one or more compounds of interest. The database may be searched to determine whether there is a match between the precursor and product ion information from step 350 and precursor and product ion information in the database. If so, the compound associated with the matching precursor and product ion information in the database is determined as the compound of interest in the sample.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A system for performing sample analysis comprising:
   an apparatus for performing solid phase extraction of a source sample to obtain a concentrated liquid sample;
   a liquid chromatograph that perform chromatographic separation of the concentrated liquid sample and generates an eluent; and
   a mass spectrometer that analyzes said eluent to detect a compound, wherein the mass spectrometer is configured to perform tandem mass spectral analysis and to detect the compound having a concentration of approximately less than one part per trillion.

2. The system of claim 1, wherein the compound is any of a pharmaceutical, personal care product, endocrine disruptor, drug, and pesticide.

3. The system of claim 1, wherein the compound is any of cimetedine, ranitidine, trimethoprim, sulfamethoxazole, 10-hydroxy-amitriptyline, promethazine, paroxetine, alprazolam, amitriptyline, benztropine, norfluoxetine, fluoxetine, desmethylsertraline, sertraline, albuterol, atenolol, clonidine, oxycodone, amphetamine, hydrocodone, triamterene, metoprolol, enalipril, propanolol, desmethyldiltiazem, diltiazem, norverapamil, verapamil, propoxyphene, amlodipine, acetaminophen, prednisone, prednisolone, hydrocortisone, carbamazepine, betamethasone, methylprednisolone, norethindrone, testosterone, valsartan, fluocinonide, atrovastatin, fluticasone, progesterone, simvastatin, theophylline, hydrochiorothiazide, 2-hydroxy-ibuprofen, furosemide, warfarin, glipizide, ibuprofen, gemfibrozil. glyburide, chlorpheniramine, tripolidine, dextromethorphan, clomitrazole, propranolol, erythromycin, terbinafine, azithromycin, miconazole, tramadol, trimethoprim, cocaine, codeine, diphenhydramine, amphetamine, tetracycline, oxytetracycline, sulfanilamide, sulfathiazole, lincomycin, cefatoxime, carbadox, ciprofloxacin, enrofloxacin, penicillin G, oxacillin, naproxen, triclosan, and atrazine.

4. The system of claim 1, wherein the source sample is any of a solid, a liquid, a food, a solid food, a liquid food, water, sludge, soil, fish tissue, animal tissue, a plant, a vegetable, a fruit, milk, honey, juice, and bird tissue.

5. The system of claim 1, wherein the source sample is any of drinking water, surface water, ground water, and wastewater.

6. A method of performing sample analysis comprising:
performing processing of a source sample, said processing including performing solid phase extraction to obtain a concentrated liquid sample;
performing liquid chromatographic separation of the concentrated liquid sample and generating an eluent; and
performing tandem mass spectral analysis of said eluent to detect a compound, wherein the compound has a concentration of approximately less than or equal to one part per trillion.

7. The method of claim 6, wherein the method is performed in a food-related industry.

8. The method of claim 6, wherein the method is performed in an environmental-related industry.

9. The method of claim 6, wherein at least one other sample processing step is performed prior to said solid phase extraction.

10. The method of claim 6, wherein said tandem mass spectral analysis is performed by a triple quadrupole mass spectrometer.

11. The method of claim 6, wherein the compound is any of a pharmaceutical, personal care product, endocrine disruptor, drug, herbicide, and pesticide.

12. The method of claim 6, wherein the compound is any of cimetedine, ranitidine, trimethoprim, sulfamethoxazole, 10-hydroxy-amitriptyline, promethazine, paroxetine, alprazolam, amitriptyline, benztropine, norfluoxetine, fluoxetine, desmethylsertraline, sertraline, albuterol, atenolol, clonidine, oxycodone, amphetamine, hydrocodone, triamterene, metoprolol, enalipril, propanolol, desmethyldiltiazem, diltiazem, norverapamil, verapamil, propoxyphene, amlodipine, acetaminophen, prednisone, prednisolone, hydrocortisone, carbamazepine, betamethasone, methylprednisolone, norethindrone, testosterone, valsartan, fluocinonide, atrovastatin, fluticasone, progesterone, simvastatin, theophylline, hydrochiorothiazide, 2-hydroxy-ibuprofen, furosemide, warfarin, glipizide, ibuprofen, gemfibrozil. glyburide, chlorpheniramine, tripolidine, dextromethorphan, clomitrazole, propranolol, erythromycin, terbinafine, azithromycin, miconazole, tramadol, trimethoprim, cocaine, codeine, diphenihydramine, amphetamine, tetracycline, oxytetracycline, sulfanilamide, sulfathiazole, lincomycin, cefatoxime, carbadox, ciprofloxacin, enrofloxacin, penicillin G, oxacillin, naproxen, triclosan, and atrazine.

13. The method of claim 6, wherein the source sample is any of a solid, a liquid, a food, a solid food, a liquid food, water, sludge, soil, fish tissue, animal tissue, a plant, a vegetable, a fruit, milk, honey, juice, and bird tissue.

14. The method of claim 6, wherein the source sample is any of drinking water, surface water, ground water, and wastewater.

15. A method of performing sample analysis comprising:
performing processing of a source sample, said processing including performing solid phase extraction to obtain a concentrated liquid sample, said source sample being other than a water sample;
performing liquid chromatographic separation of said concentrated liquid sample and generating an eluent; and
performing tandem mass spectral analysis of said eluent to detect a compound, wherein the compound has a concentration of approximately less than ten parts per trillion.

16. The method of claim 15, wherein the source sample is any of a solid, a liquid, a food, a solid food, a liquid food, sludge, soil, fish tissue, animal tissue, a plant, a vegetable, a fruit, milk, honey, juice, and bird tissue.

17. The method of claim 15, wherein the compound is any of a pharmaceutical, personal care product, endocrine disruptor, drug, and pesticide.

18. The method of claim 15, wherein the concentration is approximately within the range of two to ten parts per trillion.

19. The method of claim 18, wherein the method is performed in a food-related industry.

20. The method of claim 15, wherein the method is performed in an environmental-related industry.

21. The method of claim 15, wherein the compound is any of a metabolite, natural product, and organic compound.

22. The method of claim 21, wherein the source sample includes a plurality of compounds including said compound, and wherein each of the plurality of compounds is any of a metabolite, natural product, and organic compound detected by said performing tandem mass spectral analysis, each of said plurality of compounds having a concentration of approximately less than or equal to one part per trillion.

23. The method of claim 15, wherein the source sample includes a plurality of compounds each detected by performing said tandem mass spectral analysis, each of said plurality of compounds having a concentration of approximately less than or equal to one part per trillion.

24. The method of claim 23, wherein at least one of the plurality of compounds is any of cimetedine, ranitidine, trimethoprim, sulfamethoxazole, 10-hydroxy-amitriptyline, promethazine, paroxetine, alprazolam, amitriptyline, benztropine, norfluoxetine, fluoxetine, desmethylsertraline, sertraline, albuterol, atenolol, clonidine, oxycodone, amphetamine, hydrocodone, triamterene, metoprolol, enalipril, propanolol, desmethyldiltiazem, diltiazem, norverapamil, verapamil, propoxyphene, amlodipine, acetaminophen, prednisone, prednisolone, hydrocortisone, carbamazepine, betamethasone, methylprednisolone, norethindrone, testosterone, valsartan, fluocinonide, atrovastatin, fluticasone, progesterone, simvastatin, theophylline, hydrochiorothiazide, 2-hydroxy-ibuprofen, furosemide, warfarin, glipizide, ibuprofen, gemfibrozil. glyburide, chlorpheniramine, tripolidine, dextromethorphan, clomitrazole, propranolol, erythromycin, terbinafine, azithromycin, miconazole, tramadol, trimethoprim, cocaine, codeine, diphenihydramine, amphetamine, tetracycline, oxytetracycline, sulfanilamide, sulfathiazole, lincomycin, cefatoxime, carbadox, ciprofloxacin, enrofloxacin, penicillin G, oxacillin, naproxen, triclosan, and atrazine.

* * * * *